US009623129B2

(12) United States Patent
Gonzales et al.

(10) Patent No.: US 9,623,129 B2
(45) Date of Patent: Apr. 18, 2017

(54) METHODS AND THERAPIES FOR TREATING INFLAMMATORY CONDITIONS WITH EXPOSED COLLAGEN

(75) Inventors: Gilbert R. Gonzales, New York, NY (US); Dale DeVore, Chelmsford, MA (US); Suresh Srivastava, Setauket, NY (US)

(73) Assignee: SnIP Holdings, Inc., The Woodlands, TX (US)

(*) Notice: Subject to any disclaimer, the term of this patent is extended or adjusted under 35 U.S.C. 154(b) by 1909 days.

(21) Appl. No.: 11/534,847

(22) Filed: Sep. 25, 2006

(65) Prior Publication Data

US 2007/0071676 A1 Mar. 29, 2007

Related U.S. Application Data

(60) Provisional application No. 60/720,788, filed on Sep. 26, 2005.

(51) Int. Cl.
*A61K 51/00* (2006.01)
*A61M 36/14* (2006.01)
*A61K 51/10* (2006.01)

(52) U.S. Cl.
CPC ...... *A61K 51/1018* (2013.01); *A61K 51/1093* (2013.01); *A61K 2121/00* (2013.01)

(58) Field of Classification Search
USPC ........................................................ 424/1.49
See application file for complete search history.

(56) References Cited

U.S. PATENT DOCUMENTS

| | | | |
|---|---|---|---|
| 4,647,445 A | 3/1987 | Lees | |
| 4,660,563 A | 4/1987 | Lees | |
| 4,877,599 A | 10/1989 | Lees | |
| 4,937,067 A | 6/1990 | Lees | |
| 5,225,181 A | 7/1993 | Srivastava et al. | |
| 5,292,938 A | 3/1994 | Mease et al. | |
| 5,334,729 A | 8/1994 | Mease et al. | |
| 5,428,156 A | 6/1995 | Mease et al. | |
| 5,429,133 A | 7/1995 | Thurston et al. | |
| 5,510,466 A | 4/1996 | Krieger et al. | |
| 5,639,879 A | 6/1997 | Mease et al. | |
| 5,711,931 A | 1/1998 | Dean et al. | |
| 5,726,153 A * | 3/1998 | Lees et al. | 514/12 |
| 5,783,169 A | 7/1998 | Sweet et al. | |
| 5,811,814 A | 9/1998 | Leone et al. | |
| 5,968,477 A | 10/1999 | Kasina et al. | |
| 6,171,577 B1 | 1/2001 | Kasina et al. | |
| 6,197,278 B1 | 3/2001 | Blankenberg et al. | |
| 7,238,340 B1 * | 7/2007 | McBride et al. | 424/1.69 |
| 2003/0152513 A1 | 8/2003 | Blankenberg et al. | |

FOREIGN PATENT DOCUMENTS

WO    WO 89/10760    11/1989

OTHER PUBLICATIONS

Bode Dissertation: Characterization of Type I and Type III Collagens in Human Tissue, Chapter 2.3, Oulu, Finland 2000.*
Lammi et al. (Bone 2002, 31, 690-696).*
Rekhter (Cardiovascular Res. 1999, 41, 376-384).*
Karel (Nature 1985, 318, 470-473).*
von der Mark (CMLS 1997, 53, 539-545).*
Qaim et al. (Int. J. Appl. Radiat. Isot. 1984, 35, 645-650).*
Mausner et al. (Radiation Effects 1986, 94, 59-63).*
Fuster (Circulation 1990, 82, 47-59).*
Fuster et al., "Atherothrombosis and High-Risk Plaque," *J Am Coll Cardiol*, 2005; 46:937-954.
Sigma-Aldrich, "Monoclonal Anti-Collagen Type III, Clone FH-7A Mouse Ascites Fluid Datasheet", [Product Information], Jul. 2005, Retrieved from the Internet: <<http://www.sigmaaldrich.com/sigma/datasheet/c7805dat.pdf.>>.
International Preliminary Report on Patentability of PCT Application No. PCT/US2006/037764, issued Mar. 26, 2008, 6 pages total.
Supplementary European Search Report and European Search Opinion, EP 06815636, Apr. 13, 2011.
Dewanjee, MK et al., Identification of New Collagen Formulation with 125I-Labeled Antibody in Bovine Pericardial Tissue Valves Implanted in Calves, International Journal of Radiation Applications and Instrumentation Part B: Nuclear Medicine and Biology, Elsevier Science Publishers, New York, NY, US, vol. 13, No. 4, Jan. 1, 1986, pp. 413-422; abstract, p. 421, col. 1, lines 19-25.
Adams, PC et al., Platelet/Vessel Wall Interactions, Rheologic Factors and Thrombogenic Substrate in Acute Coronary Sytndromes: Preventive Strategies, American Journal of Cardiology, Cahners Publishing Co., Newton, MA, US, vol. 60, No. 12, Oct. 30, 1987, pp. G9-G16; abstract, p. 13G, col. 1, lines 1-5.
Penz, Sandra et al., Human atheromatous plaques stimulate thrombus formation by activating platelet glycoprotein VI, FASEB Journal, Fed. of American Soc. for Experimental Biology, US, vol. 19, No. 8, Jun. 1, 2005, pp. 898-909; abstract, p. 903.
Van Zanten, G Henrita et al., Increased platelet deposition on atherosclerotic coronary arteries, Journal of Clinical Investigation, American Society for Clinical Investigation, US, vol. 93, No. 2, Jan. 1, 1994, pp. 615-632; the whole document.
Srivastava, Suresh C., Criteria for the Selection of Radionuclides for Targeting Nuclear Antigens for Cancer Radioimmunotherapy, Cancer Biotherapy and Radiopharmaceuticals, Mary Ann Liebert, US, vol. 11, No. 1, Jan. 1, 1996, pp. 43-50; the whole document.
Massberg, Steffen, et al., Soluble glycoprotein VI dimer inhibits platelet adhesion and aggregation to the injured vessel wall in vivo, FASAB Journal, Fed. of American Soc. for Experimental Biology, US, vol. 18, No. 2, Feb. 1, 2004, pp. 397-399; the whole document.
Birchler et al., "Selective targeting and photocoagulation of ocular angiogenesis mediated by a phage-derived human antibody fragment," *Nat Biotechnol*. 1999;17:984-988.

(Continued)

*Primary Examiner* — Michael G. Hartley
*Assistant Examiner* — Melissa Perreira
(74) *Attorney, Agent, or Firm* — Wood Herron & Evans LLP

(57) ABSTRACT

Compositions and methods for treating and imaging vulnerable plaque and other inflammatory conditions in a patient rely on the delivery of conversion electron-emitting sources and other radionuclides to regions of exposed collagen in the vasculature or other body lumens. The conversion electron-emitting sources or other radionuclides are coupled to a collagen-binding substance and administered to the vasculature or other body lumen to permit binding for imaging and/or therapeutic purposes.

14 Claims, No Drawings

(56) References Cited

OTHER PUBLICATIONS

Burrone et al., "Electrical resonance and Ca2+ influx in the synaptic terminal of depolarizing bipolar cells from the goldfish retina," *J Physiol.* 1997;505:571-584.

Carnemolla et al., "Phage antibodies with pan-species recognition of the oncofoetal angiogenesis marker fibronectin ED-B domain," *Int J Cancer.* 1996;68:397-405.

Demos et al., "In-Vitro Targeting of Antibody-Conjugated Echogenic Liposomes for Site Specific Ultrasonic Image Enhancement," *J. Pharm. Sci.* 1997, 86(2):167-171.

Dinkelborg et al., "Molecular imaging of atherosclerosis using a technetium-99m-labeled endothelin derivative," *J Nucl Med.* 1998;39:1819-1822.

Elmaleh et al, "Rapid Noninvasive Detection of Experimental Atherosclerotic Lesions with Novel 99mTc-Labeled Diadenosine Tetraphosphates," *Proc. Natl. Acad. Sci.* USA, 1998, 95:691-695.

Halin et al., "Enhancement of the antitumor activity of interleukin-12 by targeted delivery to neovasculature," *Nat Biotechnol.* 2002;20:264-269.

Halin et al., "Tumor-targeting properties of antibody-vascular endothelial growth factor fusion proteins," *Int J Cancer*, 2002;102:109-116.

Kolodgie et al., Targeting of apoptotic macrophages and experimental atheroma with radiolabeled annexin V: a technique with potential for noninvasive imaging of vulnerable circulation 2003,108: 3134-3139.

Lees et al. "Imaging Human Atherosclerosis with 99mTc-Labeled Low Density Lipoproteins," (1998) *Arteriosclerosis* 8:461-470.

Matter et al, "Molecular imaging of atherosclerotic plaques using a human antibody against the extra-domain B of fibronectin," *Circ Res.* 2004;95:1225-1233.

Narula et al.,"Noninvasive Localization of Experimental Atherosclerotic Lesions With Mouse/Human Chimeric Z2D3 F(ab')2 Specific for the Proliferating Smooth Muscle Cells of Human Atheroma," *Circulation*, 1995,92: 474-484.

Neri et al., "Targeting by affinity-matured recombinant antibody fragments of an angiogenesis associated fibronectin isoform," *Nat Biotechnol.* 1997;15:1271-1275.

Nilsson et al., "Targeting delivery of tissue factor to the ED-B domain of fibronectin, a marker of angiogenesis, mediates the infarction of solid tumors in mice," *Cancer Res.* 2001;61:711-716.

Pini et al., "Design and use of a phage display library. Human antibodies with subnanomolar affinity against a marker of angiogenesis eluted from a two-dimensional gel," *J Biol Chem.* 1998;273:21769-21776.

Srivastava et al, "Progress in research on ligands, nuclides and techniques for labeling monoclonal antibodies," *Nucl Med Biol* 1991;18:589-603.

Srivastava et al., "Development and evaluation of copper-67 and samarium-153 labeled conjugates for tumor immunotherapy," *Int J Pharmacog* 1995; 33:92-101.

Srivastava et al., "Reactor production of high-specific activity tin-117m for bone pain palliation and bone cancer therapy," *J Nucl Med*, 2004; 45: 475P.

Srivastava et al., "Recent advances in radionuclide therapy," *Sem Nucl Med* 2001; 31: 330-341.

Srivastava, "Criteria for the selection of radionuclides for targeting nuclear antigens for cancer radioimmunotherapy," *Cancer Biother Radiopharm* 1996; 11: 43-50.

Srivastava, "Is there life after technetium: What is the potential for developing new broad-based radionuclides?" *Sem Nucl Med* 1996; 26: 119-131.

Stratton et al., "Selective Uptake of Radiolabeled Annexin V on Acute Porcine Left Atrial Thrombi," *Circulation* 1995, 92:3113-3121.

Vallabhajosula et al., "Atherosclerosis: Imaging Techniques and the Evolving Role of Nuclear Medicine," *J. Nucl. Med.*, 1997, 38:1788-1796.

Viti et al., "Increased binding affinity and valence of recombinant antibody fragments lead to improved targeting of tumoral angiogenesis," *Cancer Res.* 1999;59:347-352.

Winter et al., "Molecular imaging of angiogenesis in early-stage atherosclerosis with alpha(v)beta3-integrin-targeted nanoparticles," *Circulation.* 2003;108:2270-2274.

\* cited by examiner

METHODS AND THERAPIES FOR TREATING INFLAMMATORY CONDITIONS WITH EXPOSED COLLAGEN

CROSS-REFERENCES TO RELATED APPLICATIONS

This application claims the benefit of provisional application No. 60/720,788, filed on Sep. 26, 2005, the full disclosure of which is incorporated herein by reference.

The subject matter of the present application is related to that of co-pending application Ser. No. 11/428,823, filed on Jul. 5, 2006, the full disclosure of which is incorporated herein by reference.

BACKGROUND OF THE INVENTION

1. Field of the Invention

The present invention relates generally to medical methods and compositions. More particularly, the present invention relates to methods and compositions for treating and imaging regions of inflammation in body lumens, such as vulnerable plaque in the vasculature.

Coronary artery disease resulting from the build-up of atherosclerotic plaque in the coronary arteries is a leading cause of death in the United States and worldwide. The plaque build-up causes a narrowing of the artery, commonly referred to as a lesion, which reduces blood flow to the myocardium (heart muscle tissue). Myocardial infarction (better known as a heart attack) can occur when an arterial lesion abruptly closes the vessel, causing complete cessation of blood flow to portions of the myocardium. Even if abrupt closure does not occur, blood flow may decrease resulting in chronically insufficient blood flow which can cause significant tissue damage over time.

A variety of interventions have been proposed to treat coronary artery disease. For disseminated disease, the most effective treatment is usually coronary artery bypass grafting where problematic lesions in the coronary arteries are bypassed using external grafts. In cases of less severe disease, pharmaceutical treatment is often sufficient. Finally, focal disease can often be treated intravascularly using a variety of catheter-based approaches, such as balloon angioplasty, atherectomy, radiation treatment, stenting, and often combinations of these approaches.

With the variety of treatment techniques which are available, the cardiologist is faced with a challenge of selecting the particular treatment which is best suited for an individual patient. While numerous of diagnostic aids have been developed, no one technique provides all the information which is needed to select a treatment. Angiography is very effective in locating lesions in the coronary vasculature, but provides little information concerning the nature of the lesion. To provide better characterization of the lesion(s), a variety of imaging techniques have been developed for providing a more detailed view of the lesion, including intravascular ultrasound (IVUS), angioscopy, laser spectroscopy, computed tomography (CT), magnetic resonance imaging (MRI), and the like. None of these techniques, however, is completely successful in determining the exact nature of the lesion. In particular, such techniques provide little information regarding whether the plaque is stable or unstable.

Plaques which form in the coronaries and other vessels comprise inflammatory cells, smooth muscles cells, cholesterol, and fatty substances, and these materials are usually trapped between the endothelium of the vessel and the underlying smooth muscle cells. Depending on various factors, including thickness, composition, and size of the deposited materials, the plaques can be characterized as stable or unstable. The plaque is normally covered by an endothelial layer. When the endothelial layer is disrupted, the ruptured plaque releases highly thrombogenic constituent materials which are capable of activating the clotting cascade and inducing rapid and substantial coronary thrombosis. Such rupture of an unstable plaque and the resulting thrombus formation can cause unstable angina chest pain, acute myocardial infarction (heart attack), sudden coronary death, and stroke. It has recently been proposed that plaque instability, rather than the degree of plaque build-up, should be the primary determining factor for treatment selection.

A variety of approaches for distinguishing stable and unstable or "vulnerable" plaque in patients have been proposed. Some of the proposals involve detecting a slightly elevated temperature within unstable plaque resulting from inflammation. Other techniques involve exposure of the plaque to infrared light. It has also been proposed to introduce radiolabeled materials which have been shown by autoradiography to bind to stable and unstable plaque in different ways. External detection of the radiolabels, however, has limited the sensitivity of these techniques and makes it difficult to determine the precise locations of the affected regions. It would therefore be of great benefit to provide for improved radiolabels, compositions, and protocols for detecting vulnerable plaque and other inflammatory luminal conditions.

Once unstable or vulnerable plaque has been detected, it would be of significant benefit to provide methods for treating that plaque to reduce the risk of rupture and abrupt closure. Conventional intravascular treatments for stenotic lesions, such as angioplasty, atherectomy, and stenting may have only limited value in treating vulnerable plaques and in some instances might actually induce acute thrombosis at the site of the vulnerable plaque. Thus, it would be desirable to provide methods and compositions for treating vulnerable plaque to lessen the risk of rupture and abrupt closure.

2. Description of the Background Art

U.S. Pat. Nos. 6,197,278; 6,171,577 and 5,968,477 describe the preparation of radiolabeled annexins and their use for imaging thrombus in the vasculature. US2003/0152513A1 suggests the delivery of conversion electrons for intraluminal catheter imaging of vulnerable plaque. Stratton et al. (1995) Circulation 92:3113-3121, consider the use of radiolabeled annexin V for intra-arterial thrombus detection. The use of radiolabeled agents for detecting atherosclerotic lesions is described in the medical literature. See, for example, Elmaleh et al. (1998) Proc. Natl. Acad. Sci. USA 95:691-695; Vallabhajosula and Fuster (1997) J. Nucl. Med. 38:1788-1796); Demos et al. (1997) J. Pharm. Sci. 86:167-171; Narula et al. (1995) Circulation 92: 474-484; and Lees et al. (1998) Arteriosclerosis 8:461-470. U.S. Pat. No. 4,660,563, describes the injection of radio labeled lipoproteins into a patient where the lipoproteins are taken up into regions of arteriosclerotic lesions to permit early detection of those lesions using an external scintillation counter. U.S. Pat. No. 5,811,814, describes an intravascular radiation-detecting catheter. The catheter is used to locate tagged red blood cells that may accumulate, for example, in an aneurysm. U.S. Pat. No. 5,429,133, describes a laparoscopic probe for detecting radiation concentrated in solid tissue tumors. Miniature and flexible radiation detectors intended for medical use are produced by Intra-Medical LLC, Santa Monica, Calif. (www.intra-medical.com). See also U.S. Pat. Nos. 4,647,445; 4,877,599; 4,937,067; 5,510,466; 5,711,931; 5,726,153; and WO 89/10760.

The following publications some of which are referenced above are also pertinent:

Carnemolla B, Neri D, Castellani P, Leprini A, Neri G, Pini A, Winter G, Zardi L. Phage antibodies with pan-species recognition of the oncofoetal angiogenesis marker fibronectin ED-B domain. Int J Cancer. 1996; 68:397-405.

Neri D, Carnemolla B, Nissim A, Leprini A, Querze G, Balza E, Pini A, Tarli L, Halin C, Neri P, Zardi L, Winter G. Targeting by affinity-matured recombinant antibody fragments of an angiogenesis associated fibronectin isoform. Nat Biotechnol. 1997; 15:1271-1275.

Pini A, Viti F, Santucci A, Carnemolla B, Zardi L, Neri P, Neri D. Design and use of a phage display library. Human antibodies with subnanomolar affinity against a marker of angiogenesis eluted from a two-dimensional gel. J Biol Chem. 1998; 273:21769-21776.

Burrone J, Lagnado L. Electrical resonance and Ca2+ influx in the synaptic terminal of depolarizing bipolar cells from the goldfish retina. J Physiol. 1997; 505:571-584.

Viti F, Tarli L, Giovannoni L, Zardi L, Neri D. Increased binding affinity and valence of recombinant antibody fragments lead to improved targeting of tumoral angiogenesis. Cancer Res. 1999; 59:347-352.

Matter C M, Schuler P K, Alessi P, Meier P, Ricci R, Zhang D, Halin C, Castellani P, Zardi L, Hofer C K, Montani M, Neri D, Luscher T F. Molecular imaging of atherosclerotic plaques using a human antibody against the extra-domain B of fibronectin. Circ Res. 2004; 95:1225-1233.

Dinkelborg L M, Duda S H, Hanke H, Tepe G, Hilger C S, Semmler W. Molecular imaging of atherosclerosis using a technetium-99m-labeled endothelin derivative. J Nucl Med. 1998; 39:1819-1822.

Kolodgie F D, Petrov A, Virmani R, Narula N, Verjans J W, Weber D K, Hartung D, Steinmetz N, Vanderheyden J L, Vannan M A, Gold H K, Reutelingsperger C P, Hofstra L, Narula J. Targeting of apoptotic macrophages and experimental atheroma with radiolabeled annexin V: a technique with potential for noninvasive imaging of vulnerable plaque. Circulation. 2003; 108:3134-3139.

Winter P M, Morawski A M, Caruthers S D, Fuhrhop R W, Zhang H, Williams T A, Allen J S, Lacy E K, Robertson J D, Lanza G M, Wickline S A. Molecular imaging of angiogenesis in early-stage atherosclerosis with alpha(v) beta3-integrin-targeted nanoparticles. Circulation. 2003; 108:2270-2274.

Halin C, Rondini S, Nilsson F, Berndt A, Kosmehl H, Zardi L, Neri D. Enhancement of the antitumor activity of interleukin-12 by targeted delivery to neovasculature. Nat Biotechnol. 2002; 20:264-269.

Halin C, Niesner U, Villani M E, Zardi L, Neri D. Tumor-targeting properties of antibody-vascular endothelial growth factor fusion proteins. Int J Cancer. 2002; 102: 109-116.

Nilsson F, Kosmehl H, Zardi L, Neri D. Targeting delivery of tissue factor to the ED-B domain of fibronectin, a marker of angiogenesis, mediates the infarction of solid tumors in mice. Cancer Res. 2001; 61:711-716.

Birchler M, Viti F, Zardi L, Spiess B, Neri D. Selective targeting and photocoagulation of ocular angiogenesis mediated by a phage-derived human antibody fragment. Nat Biotechnol. 1999; 17:984-988.

Srivastava S. Criteria for the selection of radionuclides for targeting nuclear antigens for cancer radioimmunotherapy. Cancer Biother Radiopharm 1996; 11: 43-50.

Srivastava S. Is there life after technetium: What is the potential for developing new broad-based radionuclides? Sem Nucl Med 1996; 26: 119-131.

Srivastava S, Mausner L, Mease R, et al. Development and evaluation of copper-67 and samarium-153 labeled conjugates for tumor immunotherapy. Int J Pharmacog 1995; 33:92-101.

Srivastava S, Dadachova, E. Recent advances in radionuclide therapy. Sem Nucl Med 2001; 31: 330-341.

Srivastava S, Mease, R. Progress in research on ligands, nuclides and techniques for labeling monoclonal antibodies. Nucl Med Biol 1991; 18:589-603.

Srivastava S C, Coller B S, and Meinken G E, Radiolabeled antiplatelet monoclonal antibody for imaging in-vivo thrombi. U.S. Pat. No. 5,225,181, Jul. 6, 1993.

Mease R C, Mausner L F, and Srivastava S C, Synthesis of 4-substituted trans-1,2-diaminocyclohexyl polyaminocarboxylate metal chelating agents for the preparation of stable radiometal antibody immunoconjugates for therapy and SPECT and PET imaging. U.S. Pat. No. 5,292,938, Mar. 8, 1994.

Mease R C, Srivastava S C, and Gestin J F, Stable radiometal antibody immunoconjugates. U.S. Pat. No. 5,334,729, Aug. 2, 1994.

Mease R C, Mausner L F, Srivastava S C. Synthesis of macrocyclic polyaminocarboxylates and their use for preparing stable radiometal antibody immunoconjugates for therapy, SPECT and PET imaging. U.S. Pat. No. 5,428, 156, Jun. 27, 1995.

Mease R C, Mausner L F, Srivastava S C. Macrocylic polyaminocarboxylates for stable radiometal antibody conjugates for therapy, SPECT and PET imaging. U.S. Pat. No. 5,639,879, Jun. 17, 1997.

Sweet M P, Mease R C, and Srivastava S C. Rigid bifunctional chelating agents. U.S. Pat. No. 5,783,169; Jul. 21, 1998.

Srivastava S (Editor). *Radiolabeled Monoclonal Antibodies for Imaging and Therapy*, Plenum, New York, 1988, pp. 876.

Srivastava, S. Criteria for the selection, production, and use of radionuclides for diagnosis and radiotherapy. In: *Technetium, Rhenium, and Other Radiometals in Chemistry and Nuclear Medicine*, M. Nicolini and U. Mazzi (editors), SG Editoriali, Padova, 1999, pp. 381-391.

Srivastava S, Toporov Yu. G, Karelin E A, Vakhetov F Z, Andreev I V, Tselishev O I and Popov Yu S, Reactor production of high-specific activity tin-117m for bone pain palliation and bone cancer therapy. J Nucl Med 2004; 45: 475P.

BRIEF SUMMARY OF THE INVENTION

The present invention provides compositions, apparatus, and methods for treating and/or imaging regions of unstable or "vulnerable" plaque and other inflammatory conditions within a blood vessel or other body lumen of a patient. While the invention is particularly intended for treating vulnerable plaque within a patient's vascular system, particularly the arterial system, including the coronary, peripheral, and cerebral arterial systems, it will be appreciated that at least certain aspects of the invention will be useful for treating other inflammatory conditions in addition to vulnerable plaque and treating body lumens and other target sites in addition to the vasculature.

It has recently been reported that rupture of the thin cap of vulnerable plaque exposes the vasculature to Type I and Type III collagen. It is believed that such collagen exposure occurs early in the process of vulnerable plaque rupture at or near the beginning of the inflammatory cascade. The present invention utilizes the exposed collagen as a marker or target for specifically binding diagnostic and/or therapeutic agents and substances at or near the regions of vulnerable plaque. While the methods and compositions of the present invention are particularly suitable for treating vulnerable plaque, they will also be useful for treating other vascular conditions and/or body lumens which are subject to inflammation and hyperplasia under conditions which result in exposure of Type I and Type III collagen. Thus, in addition to treating vulnerable plaque in the arterial system, the present invention can be used to treat other conditions of the blood vessels, including inflammation and occlusion of arteriovenous fistulas (typically used for dialysis access), diseased microvascular arteries, diseased arterioles, venules (such as macular and meningorachidian vessels), and the like. The methods and compositions of the present invention will also be useful for treating other conditions in other body lumens, including ureters, urethras, the vaginal canal, the cervical os, the esophagus, the trachea, bronchioles, bronchi, the gastrointestinal tract, ostomies, biliary ducts, pancreatic ducts, and the like.

According to the present invention, vulnerable plaque and other inflammatory conditions are treated and/or imaged by introducing to the vasculature or other body lumen an amount of a collagen Type I and/or Type III binding substance bound to a radionuclide. The radionuclide will typically be a conversion electron emitting source (CEES), as defined in more detail below. In other instances, however, the radionuclide can be other than a CEES. Exemplary radionuclides intended particularly for imaging vulnerable plaque and other regions of inflammation include those set forth in Table I.

TABLE I

| | | | | | | |
|---|---|---|---|---|---|---|
| F-18 | Sc-47 | Cr-51 | Mn-52m | Fe-52 | Co-55 | Co-57 |
| Cu-62 | Cu-64 | Ga-66 | Cu-67 | Ga-67 | Ga-68 | As-72 |
| Se-75 | Br-75 | Br-76 | Br-77 | Y-86 | Zr-89 | Tc-94 |
| Tc-95m | Ru-97 | Tc-99m | In-111 | In-113m | I-123 | I-124 |
| I-125 | I-131 | Sm-153 | Lu-177 | Re-186 | Re-188 | Hg-195m |
| Pt-195m | Au-199 | Tl-201 | Pb-203 | Sn-117m | | |

Exemplary radionuclides which are suitable for the treatment of vulnerable plaque and other inflammatory conditions include those in Table II.

TABLE II

| | | | | | | |
|---|---|---|---|---|---|---|
| P-32 | P-33 | Sc-47 | Cu-64 | Cu-67 | Ga-67 | As-77 |
| Sr-89 | Y-90 | Pd-103 | Rh-105 | Pd-109 | Ag-111 | In-111 |
| Sn-117m | I-123 | I-125 | I-131 | Pr-142 | Pm-149 | Sm-153 |
| Ho-166 | Dy-166 | Er-169 | Lu-177 | Re-186 | Re-188 | Ir-192 |
| Ir-194 | Pt-195m | Hg-195m | Au-199 | Tl-201 | At-211 | Pb-212 |
| Bi-212 | Bi-213 | Ac-225 | Fm-255 | Gd-159 | | |

Vulnerable plaque and other inflammatory conditions are preferably imaged and/or treated by administering a conversion electron emitting source (CEES) to a patient. The CEES is preferably tin-117m, but can also be holmium-166, thallium-201, technitium-99m, or the like. For therapeutic purposes, the CEES will be administered at a dose sufficient to inhibit rupture of vulnerable plaque, preferably at a total intravenously administered dosage in the range from 0.05 millicuries to 20 curies, to provide for a concentration of 0.05 microcuries to 2 millicuries, more preferably in the range from 0.1 microcuries ($\mu$Ci) to 10 microcuries ($\mu$Ci) within the lesions, assuming a range of uptake into the lesion of 0.01-0.1% of the total administered dose. These numbers can be easily modified based on the efficiency of the uptake of the CEES into the lesion, if it is more or less than the assumed 0.01-0.1% of the total administered dose. For imaging, the CEES (consisting of a gamma component in its emission) will be delivered under conditions which allow it to localize at a region of vulnerable plaque or other inflammatory response, and imaging will be based on external or other detection of emitted gamma radiation from the CEES.

The CEES or other radionuclide will be bound to a binding substance capable of specifically binding to Type I and/or Type III collagen which is exposed within the body lumen as a result of the inflammatory condition, for example, as the thin cap in vulnerable plaque enters an initial (or more advanced) phase of the rupture process. Such specific binding substances will typically be antibodies or a binding fragment thereof, such as a functional antibody-binding fragment (Fab) or a single chain fragment (scFv). Polyclonal and monoclonal antibodies can be obtained from commercial sources as set forth in Table III, and converted into functional binding fragments, as necessary.

TABLE III

| | |
|---|---|
| Rabbit anti-human Type I (IgG), 100% specificity<br>MD Biosciences Inc.<br>1000 Westgate Drive, Suite 162<br>St. Paul, MN 55114, USA | Rabbit anti-human Type I<br>Rabbit anti-human Type III<br>Novotec, 243, route de Sandrancourt<br>F-78520 Saint Martin La Garenne, France |
| Mouse anti-human Type I, Rabbit anti-human Type I, Rabbit anti-human Type III-all (IgG)<br>RDI- Division of Fitzgerald Industries Int'l<br>(formerly Research Diagnostics Inc)<br>Pleasant Hill Road<br>Flanders, NJ 07836 USA | Rabbit anti-human Type I collagen, 100% specificity<br>Rabbit anti-human Type III collagen, 100% specificity<br>Karlan Research Products Corporation<br>3343 Industrial Drive, Unit 9<br>Santa Clara, CA 95403 |
| Mouse anti-human Type I collagen (IgG)<br>Southern Biotech<br>160A Oxmoor Blvd.<br>Birmingham, AL 35209 | Mouse anti-human Type I (monoclonal, IgG)<br>Mouse anti-human Type III (monoclonal, IgG)<br>Mouse anti-human Type III (IgA)<br>Abcam Inc., One Kendall Square, Bldg. 200, 3rd Floor<br>Cambridge, MA 02139 |
| Humanized anti-human collagens<br>Alexion Pharmaceuticals, Inc.<br>352 Knotter Drive<br>Cheshire, CT 06410 | Humanized anti-human Type I–IV collagen (QH2B, 2D4)<br>CancerVax, 2110 Rutherford Road<br>Carlsbad, California 92008 |
| Mouse anti-human Type III (IgG1), monoclonal, Clone FH-7A<br>ABR-Affinity Reagents<br>4260 Technology Drive<br>Golden, CO 80403 | Mouse anti-human Type I (IgG1/k), monoclonal, Clone 5D8<br>Mouse anti-human Type III (IgG1/k), monoclonal Clone 1E7<br>AntibodyShop A/A |

TABLE III-continued

| | |
|---|---|
| Mouse anti-human Type III (IgG), monoclonal Clone HWD1.1 BioGenex 4800 Norris Canyon Rd. San Ramon, CA 94583 | Grusbakken 8 DK-2820 Gentofte Denmark Rabbit anti-human Type I, polyclonal Mouse anti-human Type I (IgG1), monoclonal, Clone NFI/20 Mouse anti-human Type I (IgG), monoclonal, Clone 2F2/51 Mouse anti-human Type III (IgM), monoclonal, Clone NLI/42 Rabbit anti-human Type I/III (purified Ig), polyclonal Rabbit anti-human Type III (purified Ig), polyclonal Biogenesis, Division of MorphoSys US, Inc. PO Box 1016 Kingston NH 03848, USA |
| Mouse anti-human VLA-2 collagen receptor (IgG1), monoclonal, Clone A.1.43 Cedarlane Laboratories, LTD 5516-8$^{th}$ Line, R.R.#2 Hornby, Ontario L0P 1E0 Canada | Rabbit anti-human Type III, polyclonal Mouse anti-human Type III, (IgG1), monoclonal, Clone 4B11.1 CHEMICON International, Inc. 28820 Single Oak Drive Temecula, CA 92590 |
| Rabbit anti-human Type I (IgG), polyclonal Cell Sciences, Inc. 480 Naponset St. Bldg 12A Canton, MA 02021 | Goat anti-human Type I (IgG), polyclonal Rabbit anti-human Type I (IgG), polyclonal Rabbit anti-human Type III (IgG), polyclonal GeneTex 14785 Omicron Drive, Suite 101 San Antonio, TX 78245 |
| Goat anti-human Type I (IgG), polyclonal Rabbit anti-human Type I (IgG), polyclonal Rabbit anti-human Type III (IgG), polyclonal GeneTex 14785 Omicron Drive, Suite 101 San Antonio, TX 78245 | Rabbit anti-human Type III (IgG), polyclonal Rabbit anti-human Type I (IgG), polyclonal Novus Biologicals, Inc. P.O. Box 802 Littleton, CO 80160 |
| Mouse anti-human Type I (IgG$_{2b}$), monoclonal Clone 2A3 Mouse anti-human Type I (IgG$_{2b}$), monoclonal, Clone 4F6 Goat anti-human Type I, polyclonal Goat anti-human Type III, polyclonal Southern Biotech 160A Oxmoor Blvd. Birmingham, AL 35209 Rabbit anti-human Type I (IgG), polyclonal (several Clones) Mouse anti-human Type I (IgG1/k), monoclonal (several Clones) Goat anti-human Type I (IgG), polyclonal Rabbit anti-human Type III (IgG), polyclonal (several Clones) Mouse anti-human Type III (IgG1/k), monoclonal (several Clones) Goat anti-human Type III (IgG), polyclonal United States Biological P.O. Box 261 Swampscott, MA 01907 | Mouse anti-human Type I (IgG1), monoclonal, Clone COL-1 Mouse anti-human Type III (IgG1), monoclonal, Clone FH-71 Sigma-Aldrich 3050 Spruce Street St. Louis, MO 63103 |

In addition to the commercial sources listed above, suitable monoclonal antibodies can be prepared as amply described in the scientific literature.

The radionuclides are coupled to the specific binding substances using conventional binding protocols and techniques. The radionuclide must remain tightly bound to this antibody or other specific binding substance so that it remains stable in vivo during the administration and binding processes so that the radionuclide may remain immobilized at or in the target tissue for a time sufficient to provide for the desired imaging and/or therapy, preferably for a time equal to at least one half-life of the radionuclide, more preferably for a time equal to several half-lives of the radionuclide. Such stability may be achieved by coupling with a bifunctional chelating agent which is first covalently attached to the antibody or other binding substance to form a chelate conjugate. The chelate conjugate is then attached to the radionuclide by a chelation process. The metal-chelate complex must not undergo metal exchange or transchelation with other ligands in vivo.

Examples of particularly useful bifunctional chelating agents are such as those set forth in Table IV.

TABLE IV

Polyaminocarboxylic acids, e.g., diethylenetriamine pentaacetic acid dianhydride (DTPADA), cyclohexyl polyaminocarboxylate 4-ICE; (4-isothiocyanato cyclohexyl EDTA, or 4-isothiocyanato-trans-1,2-diaminocyclohexane-N,N,N'',N'''-tetraacetic acid), and others
Macrocycle derivatives such as C8N4 macrocycle DOTA-NHS (mono-NHS ester of 1,4,7,10, TABLE IV-continued tetraazacyclododecane N,N',N",N''' tetraacetic acid), and others
Macrocycle derivatives such as C10N4 macrocycle TETA-NHS (mono-NHS ester of 1,4,8,11-
tetraazacyclotetradecane N,N',N",N''' tetraacetic acid), and others These ligands are suitable for binding to Sn-117m and most other radiometals listed above. Many larger metal ions such as Hg and others may require multiple (>6) coordination sites and although 4-ICE and/or DOTA/TETA-NHS may prove to be moderately successful, more effective chelating agents (such as bis-CDTA) that combine increased rigidity with high denticity (coordination sites) in their structures are required. In addition, there are many other chelating agents that have recently been developed for specific metals such as Cu-67, Tc-99m, and In-111. Many of these are also expected to work with Sn-117m as well.

Compositions according to the present invention will comprise a collagen binding substance and a radionuclide, typically a conversion electron emitting source, preferably tin-117m or one of the other CEES's listed above. The collagen binding substance may be any of those substances listed in Tables III and IV above. Preferred compositions will be prepared using the tin-117m metal or other CEES that will typically have a specific activity ranging between 0.5 curies per gram and 10,000 curies per gram, preferably being about 1000 curies per gram. These compositions are suitable for both therapeutic treatment and imaging of vulnerable plaque according to the methods described above.

DETAILED DESCRIPTION OF THE INVENTION

The present invention provides for the administration of conversion electron emitting sources (CEES) and other radionuclides to patients for therapeutic and diagnostic purposes. The CEES's will be coupled to a Type I or Type III collagen-binding substance to enhance localization at regions of vulnerable plaque or other inflammatory regions. Pharmaceutical therapeutic compositions according to the present invention can be administered to any patient, including humans and animals, by parenteral, systemic, or local injections into vasculature or other locations, including the epidural, the subarachnoid compartment, solid tissue, the pulmonary system, the reticuloendothelial system, potential cavities, and the like. The compositions and methods will be suitable for imaging atherosclerotic atheroma, commonly referred to as hard plaque, as well as soft or vulnerable plaque, although treatment will be particularly effective for the soft or vulnerable plaque.

Imaging will rely on the detection of gamma photon emission from the CEES's. The imaging will typically be external, e.g. using a planar or SPECT gamma camera or another suitable detector placed on or over the patient's skin or over a target body organ, but could in some places be local, e.g. using a catheter or other intravascular, intraluminal, or tissue-penetrating probe.

The CEES may be any medically compatible radionuclide but will preferably be tin-117m which primarily emits conversion electrons, but in some cases could also be Ga-67, I-123, holmium-166, thallium-201, or technetium-99m which have different-range or differently effective conversion electron emissions, and a gamma photon component. The tin-117m will preferably be in metallic form and can be prepared in an accelerator, such as a linear accelerator or a cyclotron, by, for example, transmutation of antimony into known No-Carrier-Added tin-117m by intermediate to high energy proton induced reactions. Alternatively, thermal or fast neutron bombardment of tin-116 or tin-117 can be performed in a reactor to produce tin-117m. The production of tin-117m is well known in the art and does not form part of the present invention.

In the compositions of the present invention, the tin-117m or other CEES is coupled, attached, or otherwise bound to a substance which preferentially or specifically binds to Type I or Type III collagen which is exposed to the vasculature at regions of vulnerable plaque or other inflammatory sites for diagnostic or therapeutic purposes. Suitable preferential binding substances are set forth in Table V above.

The storage time for the CEES in the compositions of the present invention can be increased by either increasing the specific activity of the tin-117m/mg or by increasing the concentration of the tin-117m in the compositions to allow for the radioactive decay. Monthly preparation, and distribution of compositions throughout the month, to cardiovascular use-centers, such as hospitals or local distribution centers, are possible. Each composition batch would have a 3 to 5 day window-of-use with differential (quantitative) CEES dosages and this will accomplish adequate availability for use so that shipping can be performed on a monthly or 2 week basis. For example, if a first batch has a 5 day usability window from the time of delivery to the cardiovascular use-center until the time the composition must be put into a human coronary artery, this composition would have a set mCi/mm and mCi/mg level of radioactivity placed on it for calendar days 1 through 5; for example usability days March 1 through 5. For a second batch delivered on the first day of March but for use on days 6 though 10 of the month, the radioactivity level of plating or deposition would be that of first batch plus the average decay for 5 days so that on day 6 of March, the batch would have the same radioactivity as the first batch on March 1. On March 1 a batch for use on March 10 through March 15 would also be delivered but would have radioactivities of tin-117m as that of the first batch plus enough tin-117m to compensate for 10 days of decay so that the third batch would have the same radioactivity on day 10 of March as the first batch has on day 1 of March. The fourth through sixth batches would have proportionally larger amounts of tin-117m in them to equal the radioactivity as the first batch for use on its first designated and approved day. In this example a total of six batches could be delivered on the first part of each month with each batch implantable for successive five day intervals during the month.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of treating an inflammatory condition in a body lumen, said method comprising:
introducing to the body lumen a therapeutically effective amount of a collagen Type I and/or Type III binding substance bound to no-carrier-added tin-117m during a cascading rupture of vulnerable plaque;

wherein the binding substance specifically binds to Type I and/or Type III collagen exposed within the body lumen as a result of the rupture of vulnerable plaque and wherein the tin-117 m provides therapy to the vulnerable plaque.

2. A method as in claim 1, wherein the collagen binding substance comprises an antibody or a fragment of an antibody that specifically binds to Type I or Type III collagen.

3. A method as in claim 2, wherein the antibody is a polycolonal antibody.

4. A method as in claim 2, wherein the antibody is a monoclonal antibody or a fragment of a monoclonal antibody that specifically binds to Type I or Type III collagen.

5. A method as in claim 4, wherein the monoclonal antibody is selected from the group consisting of the monoclonal antibodies listed in Table III.

6. A method as in claim 5, wherein the tin-117m has a specific activity of between 0.5 curies per gram and 10,000 curies per gram.

7. A method as in claim 6, wherein the tin-117m is in a therapeutic dosage form having a total radiation concentration in the lesions in the range from 0.1 $\rho$Ci to 10 mCi.

8. A method as in claim 5, further comprising detecting gamma radiation to localize a region of inflammation.

9. A method as in claim 1, wherein the inflammatory condition is a region of vulnerable plaque in a patient's vasculature.

10. A method as in claim 1, wherein the collagen binding substance and the tin-117m are directly bound.

11. A method as in claim 1, wherein the collagen binding substance and the tin-117m are bound by a linking agent.

12. A method as in claim 11, wherein the linking agent comprises a bifunctional chelating agent.

13. A method as in claim 12, wherein the bifunctional chelating agent is selected from the group consisting of the agents in Table IV.

14. A method as in claim 1, wherein the collagen binding substance comprises a substance which specifically binds Type I and Type III collagen.

\* \* \* \* \*